United States Patent [19]

Bacus

[11] Patent Number: 4,741,043
[45] Date of Patent: Apr. 26, 1988

[54] METHOD OF AND AN APPARATUS FOR IMAGE ANALYSES OF BIOLOGICAL SPECIMENS

[75] Inventor: James W. Bacus, Hinsdale, Ill.

[73] Assignee: Cell Analysis Systems, Inc., Chicago, Ill.

[21] Appl. No.: 794,937

[22] Filed: Nov. 4, 1985

[51] Int. Cl.⁴ .............................................. G06K 9/00
[52] U.S. Cl. ........................................ 382/6; 128/633; 350/534; 356/39; 358/107; 364/416
[58] Field of Search ................... 382/6; 356/39–40; 377/10; 364/416, 413; 358/107, 93; 350/534, 535, 536, 507, 529, 531; 206/456; 424/3; 427/2; 128/633

[56] References Cited

U.S. PATENT DOCUMENTS

| | | | |
|---|---|---|---|
| 3,297,879 | 1/1967 | Meyer | 382/61 |
| 3,481,659 | 12/1969 | Rosenberg | 350/94 |
| 3,847,486 | 11/1974 | McCabe | 356/205 |
| 3,907,437 | 9/1975 | Hirschfeld | 356/39 |
| 3,977,791 | 8/1976 | Weber et al. | 356/168 |
| 4,000,417 | 12/1976 | Adkisson et al. | 356/39 |
| 4,017,192 | 4/1977 | Rosenthal | 356/39 |
| 4,045,772 | 8/1977 | Bouton et al. | 340/146.3 |
| 4,048,616 | 9/1977 | Hart et al. | 340/146.3 |
| 4,097,845 | 6/1978 | Bacus | 340/146.3 |
| 4,125,828 | 11/1978 | Resnick et al. | 340/146.3 |
| 4,129,854 | 12/1978 | Suzuki et al. | 382/6 |
| 4,174,178 | 11/1979 | Ouchi et al. | 356/39 |
| 4,175,860 | 11/1979 | Bacus | 356/39 |
| 4,199,748 | 4/1980 | Bacus | 340/146.3 |
| 4,207,554 | 1/1980 | Resnick et al. | 382/6 |
| 4,213,036 | 7/1980 | Kopp et al. | 235/92 |
| 4,219,440 | 8/1980 | Runck et al. | 252/408 |
| 4,227,814 | 10/1980 | Soodak et al. | 356/410 |
| 4,232,970 | 11/1980 | Sawamura et al. | 356/432 |
| 4,257,709 | 3/1981 | Mostyn, Jr. | 356/40 |
| 4,307,376 | 12/1981 | Miller et al. | 340/146.3 |
| 4,362,386 | 12/1982 | Matsushita et al. | 356/39 |
| 4,389,669 | 6/1983 | Epstein et al. | 358/101 |
| 4,404,683 | 9/1983 | Kobayashi et al. | 382/6 |
| 4,408,231 | 10/1983 | Bushaw et al. | 382/50 |
| 4,446,871 | 5/1984 | Imura | 128/633 |
| 4,453,266 | 6/1984 | Bacus | 382/6 |
| 4,513,438 | 4/1985 | Graham et al. | 382/6 |
| 4,523,278 | 6/1985 | Reinhardt et al. | 364/413 |
| 4,562,593 | 12/1985 | Ooe et al. | 382/6 |
| 4,592,089 | 5/1986 | Hartman | 382/6 |

FOREIGN PATENT DOCUMENTS

0088716  5/1984  Japan ................................ 350/535

Primary Examiner—Leo H. Boudreau
Attorney, Agent, or Firm—Fitch, Even, Tabin & Flannery

[57] ABSTRACT

A user interactive system for dynamically testing and evaluating various cells, antigens, or other materials taken from the human body. More specifically, the DNA in specimen cells is analyzed and quantified by image analysis using pattern recognition techniques. The user is provided with a unique slide or support on which there are specimen and reference materials or objects which are simultaneously stained or otherwise image enhanced at the time of analysis.

58 Claims, 6 Drawing Sheets

FIG. 7
DNA PLOIDY ANALYSIS
LIGHT SOURCE CALIBRATION

FIG. 3A
CASE HISTORIES FOR LYMPHOMAS

CASE 1
A 60 YEAR OLD MALE PRESENTING WITH DIFFUSE LARGE CELL LYMPHOMA PRIMARY IN THE COLON. CLINICAL EVALUATION INDICATED THE PATIENT WAS STAGE IIA. THE PATIENT WAS TREATED WITH CHEMOTHERAPY AND RADIATION THERAPY AND ACHIEVED A COMPLETE RESPONSE. HOWEVER, 1-1/2 YEARS AFTER THE INITIAL THERAPY THE PATIENT RELAPSED AND SUBSEQUENT THERAPY COULD NOT ACHIEVE COMPLETE REMISSION. THE PATIENT DIED 3-1/2 YEARS AFTER INITIAL DIAGNOSIS.

DNA HISTOGRAM OF DHL. FEULGEN DEPARAFINIZED DISAGGREGATED PREPARATION—NOTE THE ABNORMAL AMOUNT OF DNA (ANEUPLOIDY OF G1) DNA INDEX 1.31 AS COMPARED TO NORMAL LYMPHOCYTES IN THE SAMPLE

FIG.3B

CASE 2

A 27 YEAR OLD FEMALE WITH DIFFUSE LARGE CELL LYMPHOMA PRESENTING IN THE CERVICAL NODES. PATIENT WAS CLINICALLY EVALUATED TO BE STAGE IIIB. THE PATIENT WAS TREATED WITH CHEMOTHERAPY AND ACHIEVED COMPLETE REMISSION. THE PATIENT HAS SURVIVED FOUR YEARS AFTER THE INITIAL DIAGNOSIS AND HAS SHOWN NO RELAPSE.

METHOD OF AND AN APPARATUS FOR IMAGE ANALYSES OF BIOLOGICAL SPECIMENS

This invention relates to a method and apparatus for clinically testing and quantifying biological specimens such as cells with image analysis of the specimens.

BACKGROUND OF THE INVENTION

The present invention is directed to a quantative testing and apparatus and method which may be used for a wide range of diagnostic testing and evaluation of various cells, antigens, or other materials taken from the human body. However, for purposes of illustration and for ease of understanding of the invention, it will be disclosed in conjunction with the preferred use thereof which is the measurement of cellular DNA for the purpose of cancer diagnosis and prognosis. More specifically, the present invention is directed to the use of image analysis using pattern recognition techniques to analyze and quantify the DNA in specimen cells taken from a person.

As will be explained in greater detail, the present invention is directed to providing equipment of a user interactive nature for use not only by researchers but also by a pathologist in a laboratory and to low-cost equipment which can be acquired by a typical pathologist laboratory.

The current state of the art in pathology laboratory is to measure the DNA content by the visual observation of the pathologist who observes primarily the shape and texture of suspected cancer cells and who then classifies the cells into a normal category or into one of several abnormal cancer categories. However, such evaluations are very subjective and can not differentiate and quantify small changes in DNA within individual cells or in very small populations of abnormal cells, which changes may represent an incipient stage of cancer or a change in cell structure due to treatment of the cancer by chemotherapy or radiation. Although there are commercially available general purpose flow cytometers, which are very expensive units and which can handle liquid blood specimens or tissue dissagregations, these cytometers are incapable of working on standard tissue sections and of using microscope slides which are the preferred specimen forms used in pathology laboratories. Additionally, the image analysis technique allows analysis of morphological features of cells such texture, size and shape of cell nuclei and alterations in nuclear-to-cytoplasmic ratios of cells whereas the flow cytometer does not allow such analysis.

When the apparatus is used for DNA analysis, tissue and cell specimens are applied to a slide which is then stained with a specific stain that combines proportionately the DNA and essentially renders invisible the remainder of the cell so that the image analysis measures DNA which is concentrated principally at the nucleus of the cell. The stain associates with the DNA to provide a detailed nuclear structure and pattern which may be visually observed and interpreted by the pathologist using the apparatus. The amount of DNA in the malignant cells is substantially greater than that for normal cells because the malignant cells are usually dividing and replicating rapidly or the malignant cells have abnormal numbers of chromosomes or have defective chromosomes.

The preferred and illustrated apparatus of the present invention can not only detect minute alterations in the nucleus by providing a real and accurate measurement of the DNA in picograms but also can measure and quantify the amount of DNA and relate it to stored statistical analyses to aid in the diagnosis. More specifically, the invention allows an iterative analysis of specimen population cells and provides a histogram or display of the population distribution of the cells with respect to their DNA content and with respect to a standard DNA for normal cells so that subtle shifts in population distribution can be readily understood. To this end cell nuclei images are not only acquired and stored but the data therefrom can be integrated with statistical data to provide multivariate analysis, discrimination of cells, histograms, and scattergrams of cells or cell populations.

However, the use of image analysis techniques and equipment and stained specimens by pathologists in a conventional pathology laboratory involves solving a number of problems which have been overcome by the present invention. For example, while there are a number of available staining techniques which can be used such as an Azure A. Feulgen staining technique described hereinafter, the staining of the DNA will vary substantially not only from slide to slide or from batch to batch by the same pathologist but will vary substantially between different pathologists and different laboratories. Because the image analysis equipment is measuring grey level or optical densities and because it is desired to provide a true actual density of DNA in picograms, it is important to overcome the problem of different staining factors for different specimens. Also, the image analysis technique uses microscopes and optical lighting which are adjustable to provide different intensities of light when used by the pathologist. Trained researchers, in research laboratories may be equipped to adjust the optical intensity to the desired conditions for image analysis by image pattern techniques but this generally will not be accomplished with the precision necessary in the usual pathology laboratory. Thus, there is a need to overcome the problem of this optical density variable.

Additionally, the present invention is directed to overcoming the problem of high costs heretofore associated with computerized equipment used for image analysis; and to this end, the present invention is an interactive system in which the pathologist performs a number of tasks and performs the preparation of cells and their selection by manipulation of the equipment. The pathologist also is provided with slides which are especially prepared and calibrated with reference cells to aid in the diagnosis of the specimen cells and to assist in overcoming the staining density problem above-described. The present invention has particularly been developed not only to locate cells for examination as to their morphology but also to preserve their location for a later analysis or corraborating analysis by a second pathologist when so desired. As will be explained, with respect to nuclei, measurements may be obtained as to area in microns, total nuclear optical density or nuclear mass in picograms, average nuclear optical density, nuclear texture, and deviation of the nuclear shape from being a round nucleus. Also, a number of such measurements may be made of the cell cytoplasm.

Accordingly, a general object of the invention is to provide a new and improved method and apparatus for analyzing cells or other biological materials by using image analysis techniques.

Another object of the invention is to provide a new and improved method and apparatus for making a ploidy analysis of cells using image pattern recognition equipment.

A further object of the invention is to provide a new and improved slide or support for specimen cells having reference cells or cell objects thereon which are used for calibrating the image analysis equipment.

These and other objects and advantages of the invention will become apparent from the following description taken in connection with the accomplishing drawings.

DETAILED DESCRIPTION OF THE DRAWINGS

DETAILED DESCRIPTION OF THE PREFERRED EMBODIMENTS

As shown in the drawings for purposes of illustration, the invention is embodied in a method and apparatus for automatically analyzing "cell objects" which term is used herein to be generic to cells, such as blood cells or cells taken from tumors, or the like, which are checked for their DNA content and to be generic to non-biological objects such as plastic or glass spheres, or to painted cell images on a slide, or to antigens or monoclonal antibodies. In systems where a monoclonal antibody is conjugated with a stain and wherein the stain may be a fluorescent material which is excited at a wave length which then can be analyzed at another wave length at which the fluorescence occurs. By way of example, the present invention is useful for study not only of ploidy analysis and blood cell analysis but also can be used to analyze pap smear cells, monoclonal antibodies, and other infectious diseases which can be diagnosed by DNA probes for viruses.

Figure 1:
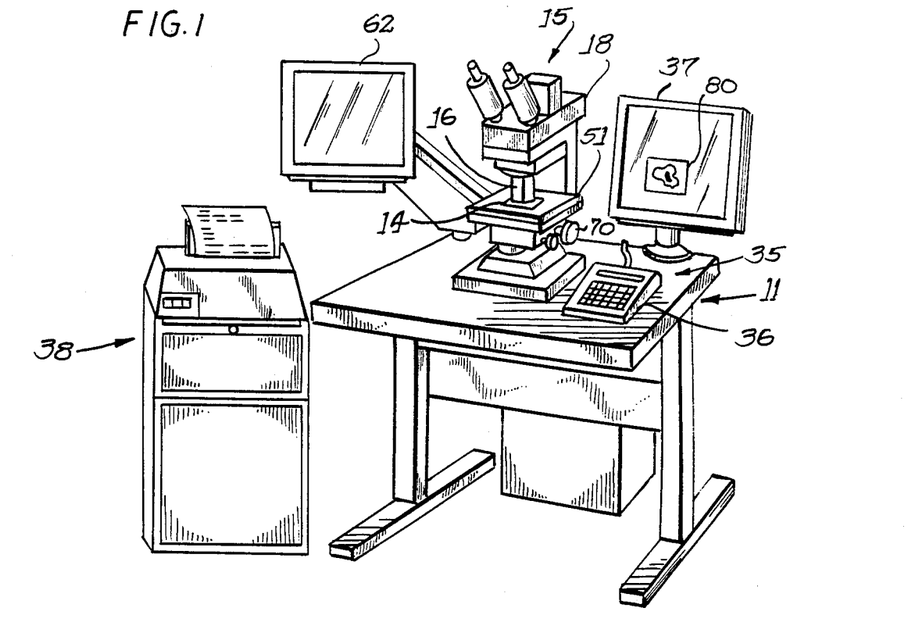
FIG. 1 is a perspective view of an apparatus constructed in accordance with the invention.
Figure 2:
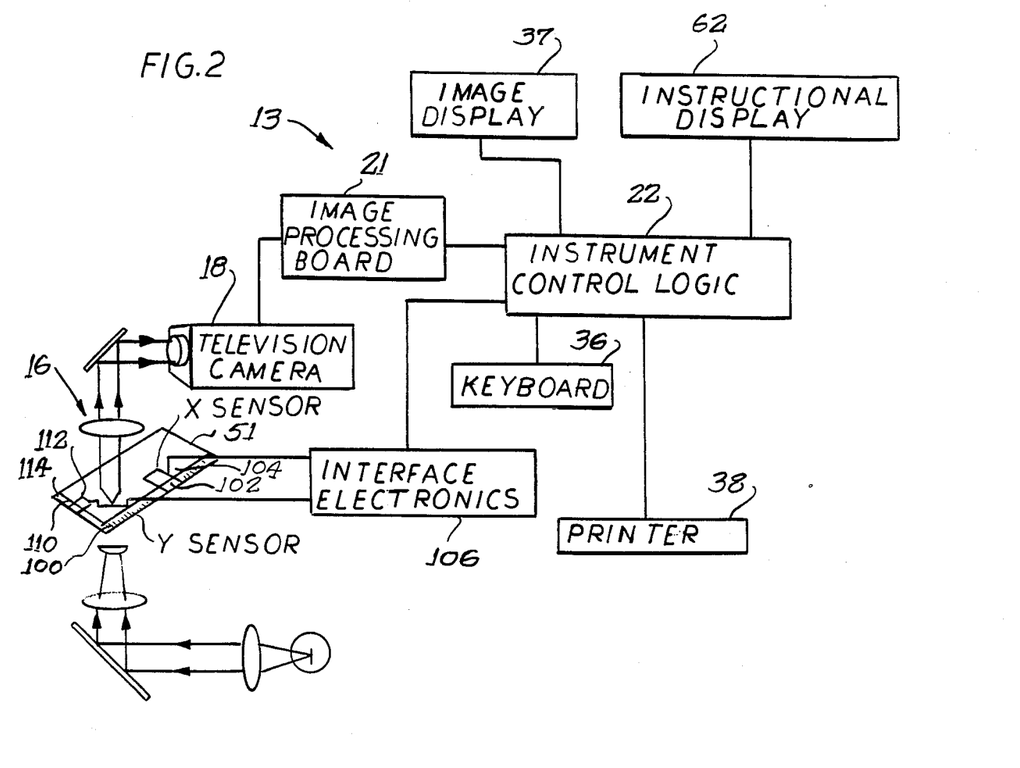
FIG. 2 is a diagramatic representation of the apparatus of FIG. 1.
Figure 2A:
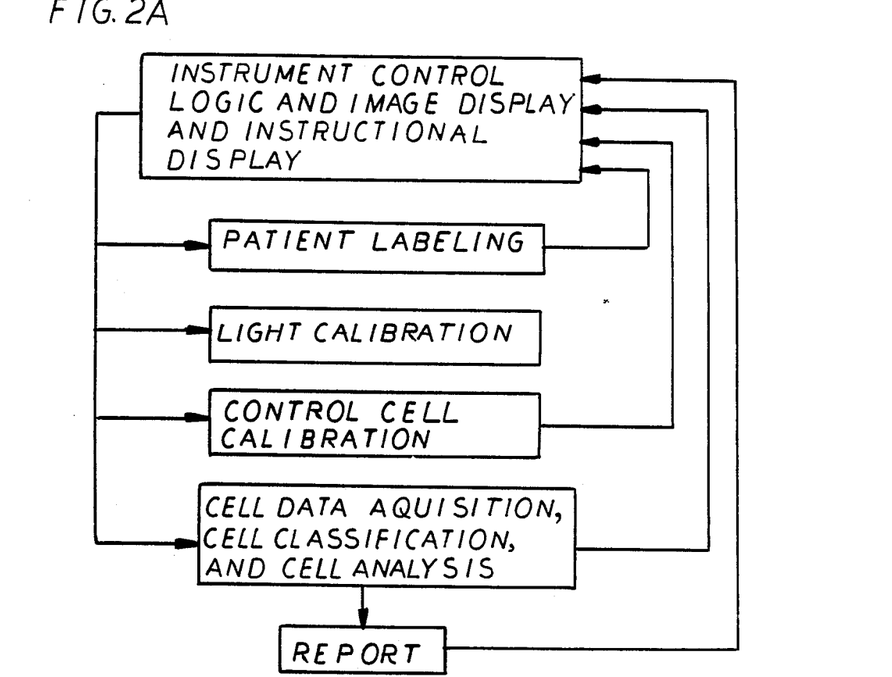
FIG. 2A is a block diagram of the operation of the apparatus of FIG. 1.
Figure 3A:
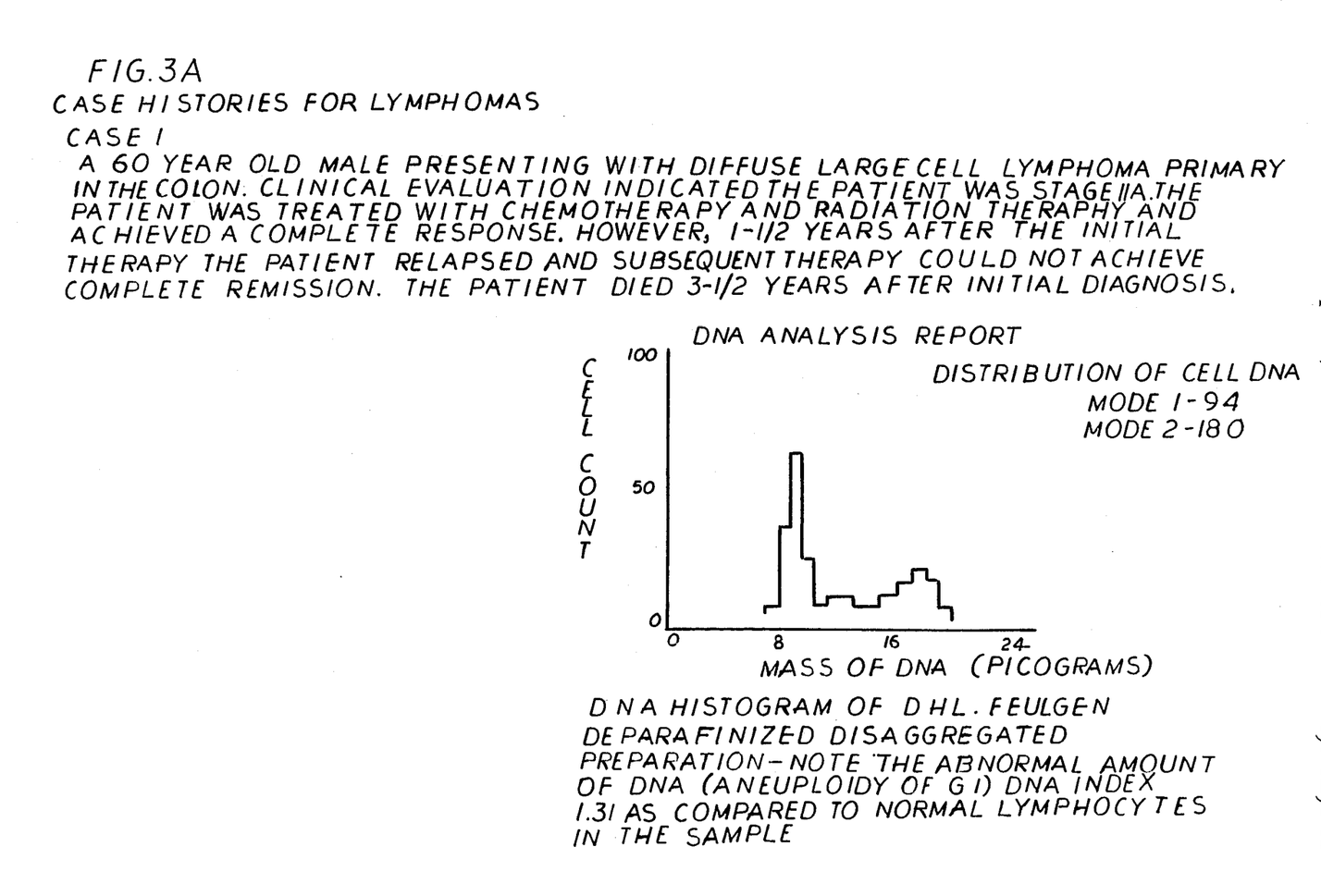
FIG. 3a is a histogram of a case history for lymphomas.
Figure 3B:
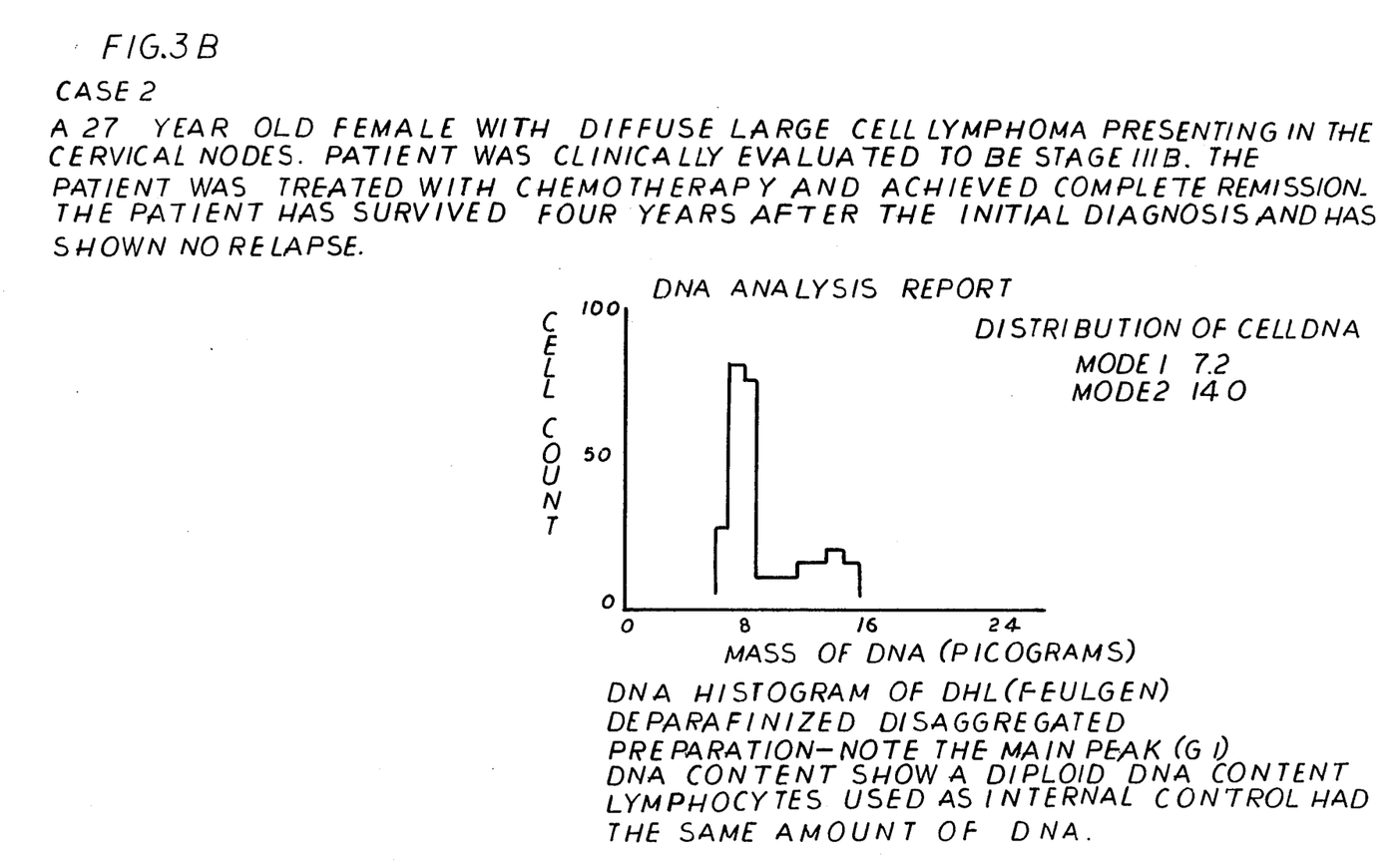
FIG. 3b is a histogram of a second case history of cell lymphomas.
Figure 7:
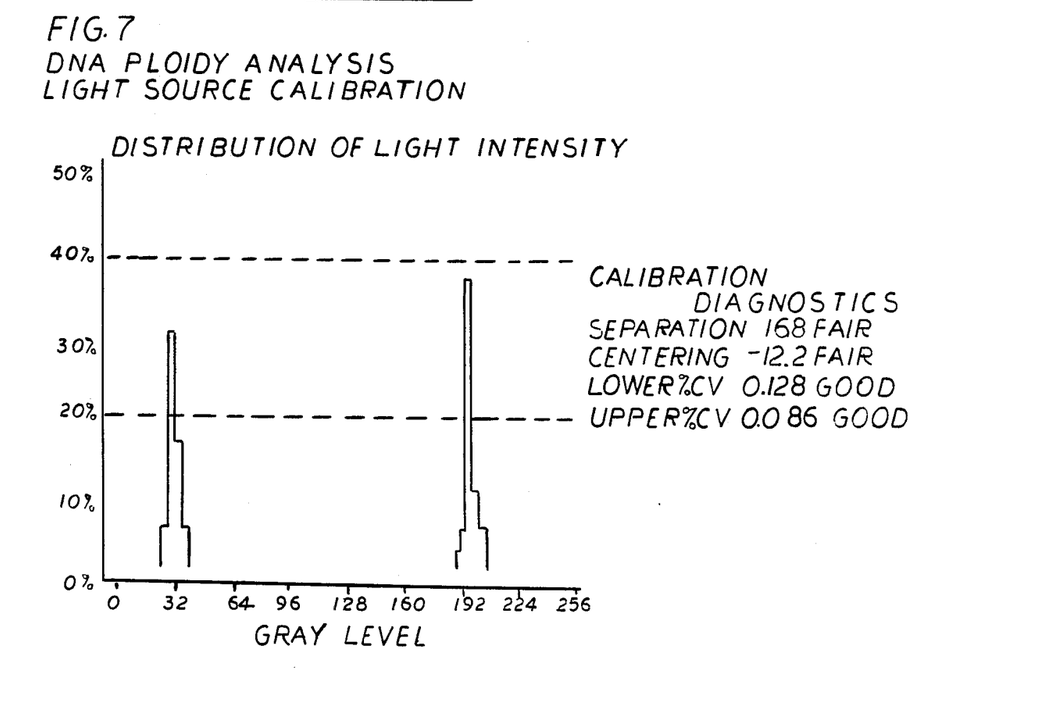
FIG. 7 is a histogram of a light source calibration made in accordance with the invention.
Figure 8:
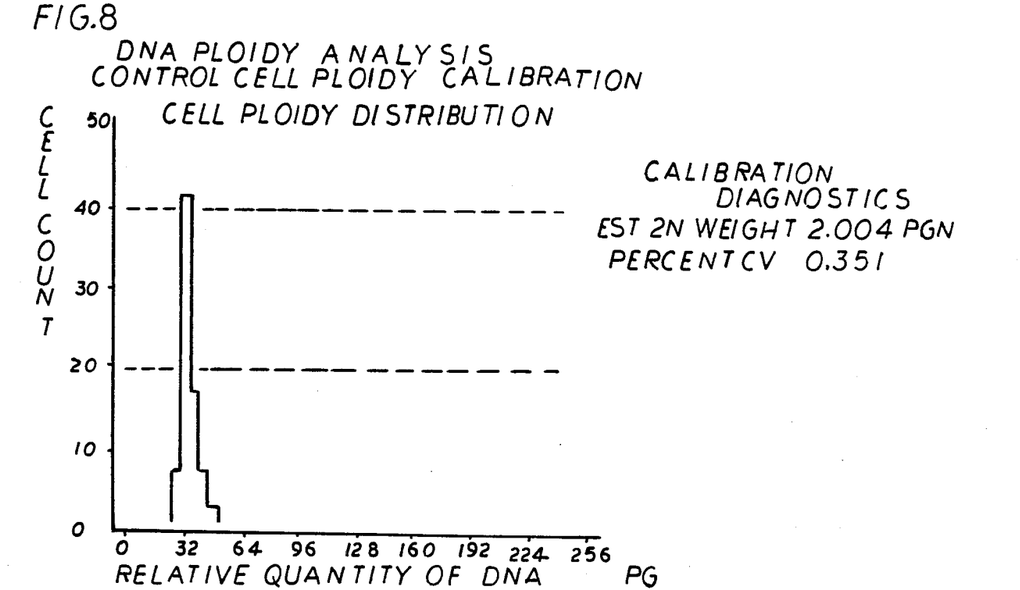
FIG. 8 is a histogram of control cell ploidy calibration made in accordance with the invention.
Figure 9:
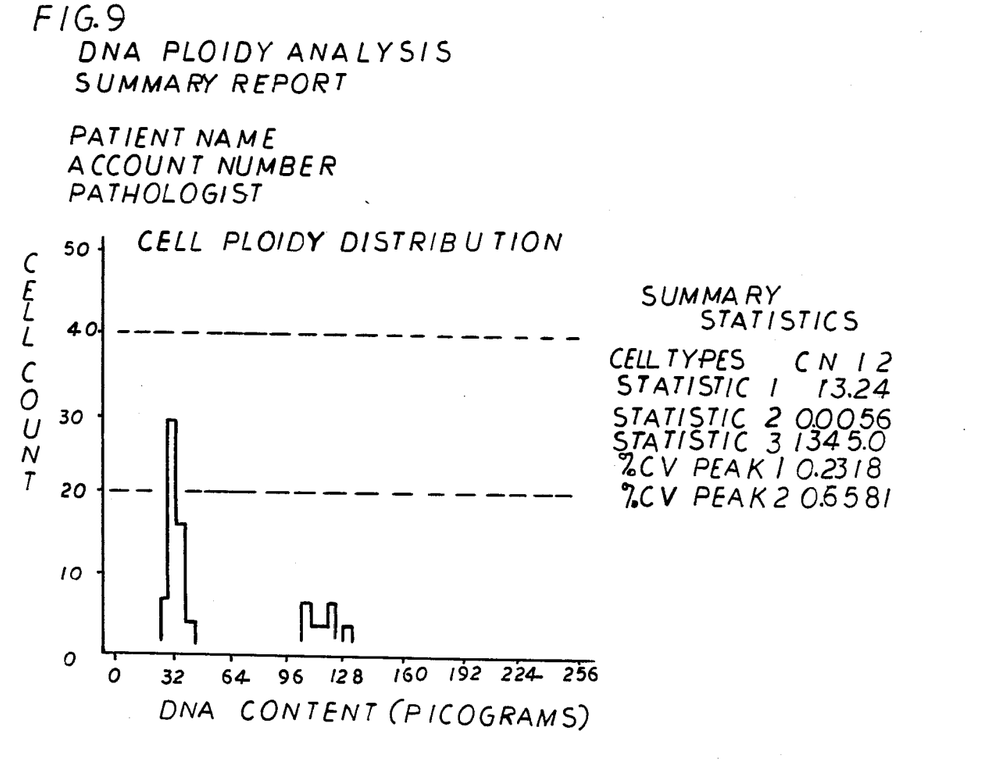
FIG. 9 is a histogram of a summary report of cell ploidy distribution in accordance with the invention.

As shown in FIGS. 1 and 2 of the drawings for purposes of illustration, the invention is embodied in an apparatus 11 having a microscopic digital image processing and pattern recognition system 13 (FIG. 2) which analyzes specimen cell objects 12 on a support or slide 14 which is preferably in the form of a glass microscope slide. Suitable high resolution microscope optics 16 (FIG. 1) provides the light to form an optical image for each of the cell objects on the slide 14. The cell objects are viewed by a solid state sensing television camera, or other detector 18 which converts the optical images point by point into a scanned electronic charge distribution representing the optical intensity of the points in each image. The output of the camera is applied to an analog to digital converter which is connected to analysis and measurement logic in an image processing board 21, which receives and stores the digitized cell images and which also contains the analysis and measurement logic to operate on the digitized cell analysis for classifying the cells as will be described hereinafter. The analysis of the shape and size as well as hemoglobin content of the cells when examining red blood cells may be accomplished in accordance with the pattern recognition technique and analysis disclosed in the inventor's U.S. Pat. Nos. 4,097,845 and 4,199,748 which are hereby incorporated by reference as if fully reproduced herein. The focus of the microscope 15 is performed manually. A terminal 35 is connected to an instrument control logic 22 and has a keyboard 36 for inputting information about the specimen or for inputting instructions to the instrument control logic 22. A monitoring screen 37 shows the cell objects and provides a visual display for the operator to review and allows the operator to select different fields for analysis and to select individual cells for classification and other analysis, as well be explained hereinafter. A written printout, such as shown in FIGS. 7–9, may also be made by a printer means 38 to afford a permanent record of the results.

Because the apparatus 11 may be used in various offices such as pathology offices having persons of varying degrees of skill and knowledge about image analysis, the microscope optical lighting 16 may be variously adjusted by different operators such that the background may have a different light intensity not only from machine to machine but also at different times depending on the age and nature of the lamp doing the illumination. When the cell objects are DNA nucleus, the stained nucleus appear darker and have high darker gray levels than the cells which have fewer or no DNA content. The particular light intensity level is desired to be known in an accurate and real manner; and hence, it is important that there be a calibration of the light intensity to eliminate errors which might be introduced if differences in light intensity levels were not accounted for. A further problem with widespread usage of equipment of the foregoing kind is the staining factor by which is meant that the user may be applying either a heavy amount or a light amount of stain which thereby also results in a variation of the gray level being viewed through a microscope 15 by the camera and then analyzed as to the particular DNA content, or the like. Thus, there is a need that the apparatus be calibrated to eliminate differences because of the staining factor so as to provide a true indication of the actual amount of hemoglobin, DNA, or antigens, monoclinial antibodies, etc. being analyzed.

In accordance with the present invention, calibration material (FIG. 5) is provided on the slide 14 which, when viewed, by the operator under a calibration step allows the operator to adjust and to calibrate the apparatus prior to the measuring and analyzing of the specimen cell objects 12 on the slide 14. In this preferred and illustrated embodiment of the invention there are provided two different calibrating materials on the slide with the first calibrating material being the control cell objects 40 which are stained simultaneously with the staining of the specimen cell objects 42, so that the analysis of the control cell objects can be compared to a predetermined stored reference light intensity, or gray level, or optical intensity which the control cell objects 40 would have after staining. If the cell objects are stained either too lightly or too heavily, the amount of understaining or overstaining can be quantatively analyzed and adjusted for as will be described hereinafter. In the preferred embodiment of the invention, the calibration material also includes an optical density reference material 45 which is usually a printed mark on the slide which has a predetermined known optical density, which can be used as a reference to calibrate the instrument. As will be explained in greater detail hereinafter, a histogram and instructions are provided to the operator from the instruction control logic to the operator and the operator manually adjusts the optical light intensity until the desired intensity is obtained for the reference material 45, and the background light. As will be explained hereinafter, the system logic is calibrated to read the proper optical density of objects.

Figure 4:
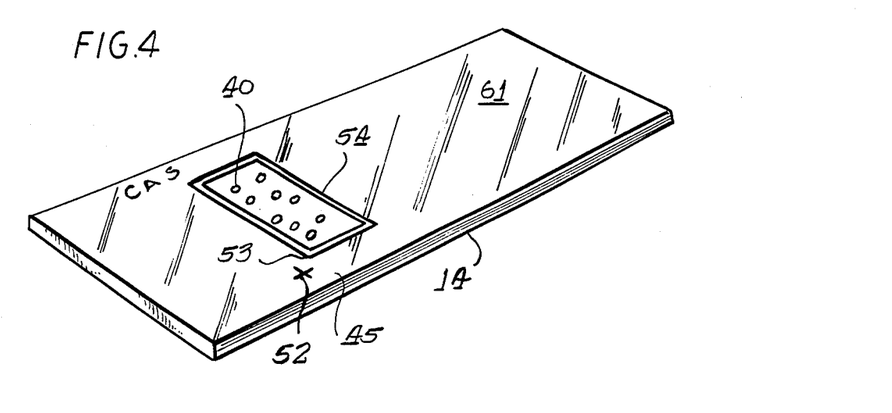
FIG. 4 is a view of a specimen slide or support constructed in accordance with the invention.
Figure 5:
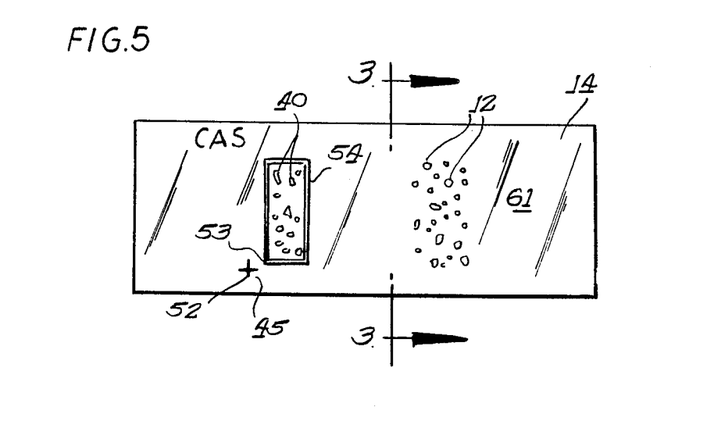
FIG. 5 is a plan view of a slide with materials thereon for control cells, specimen cells, light calibration, reference location, and integrity checking.
Figure 6:
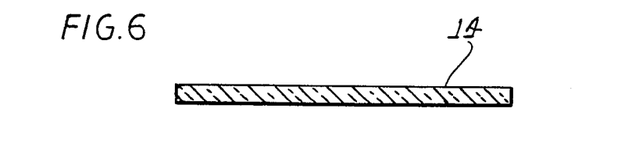
FIG. 6 is a cross sectional view taken along the line 4—4 in FIG. 3.

As a safeguard to the integrity of the system, it is desired to provide an integrity check or identification from the slide 14 by analyzing a predetermined and prefixed optical pattern on the slide which is read and measured as to gray levels and physical dimensions before the analyzing may be begun. Herein, the optical integrity pattern may be in the form of initials CAS located above the control cell objects as seen in FIGS. 4 and 5. Manifestly, the integrity check may be the cross 45 or any other material on the slide 14.

The present invention is also useful for later analysis of the specimen cells 12 on the slide 14; and to aid in the recall of cell images stored in memory or to allow the operator or another person to return to a given cell for a second review thereof at a later time. To this end, after the slide 14 has been secured on the microscope stage 51 (FIG. 1) a certain location on the slide, such as the center 52 of the cross 45, is noted as the zero-zero X-Y reference point; then the location registers for the X and Y distances are zeroed at this point so that subsequently all cell locations may have a specific X and Y coordinate address from the center 52 of the cross. A further easy location to find with the adjustment with the microscope stage 51 is a corner such as the right-hand lower corner 53 of the box border 54 within which are located the reference cell objects 40. Herein, the box border 54 is printed on the slide and it also may be used for optical density calibration rather than the special cross 45. On the other hand, by suitable logic and control, any point on the slide and microscope stage at which the classification operation begins may be taken as the zero X and Y location with the location registers for the X and Y coordinates being zeroed initially at this location and then providing a readout for each cell location from this zeroed location.

Turning now in greater detail to the preferred embodiment of the invention, the specimens slide 14 may be of any size or shape but because of the familiarity of lab technicians and pathologists with glass slides used with microscopes, it is preferred that the support 14 be an actual microscope slide of glass which typically measures 3 inch by 1 inch. The illustrated slide 14 shown in FIG. 4 has a preprinted border 54 within which are located the reference cell objects 40. The control cell objects are, in this illustrated embodiment of the invention, lymphoblastoid cells of a known size and shape and DNA content. The lymphoblastoid cells may be mostly of the type having normal DNA content, although some cells may have double or other ratios to the normal DNA content which is typical of cancer cells. The control cell objects may be other types of cells having dark centers or nuclei which stain well, such as chicken blood cells. On the other hand, the cell objects 40 may be artifacts printed on the slide to have a cell shape. Furthermore, as above explained, the cell objects 40 may, in fact, be well known plastic beads of a predetermined size which will react with a particular flourescent stain or enzyme stain when treated simultaneously with specimen cell objects such as monoclonal antibodies used in the specimen area 61 of the slide. The reference cell objects will vary from test to test and the present invention is not limited to any particular test or cell objects therefor. The pathologist will take a previously prepared slide such as shown in FIG. 4 having premounted thereon the control cell objects 40 and add thereto the specimen cell objects 12 which are, in this instance, cells from a slice of tissue (such a tumor tissue), or a a needle aspirate of tumor tissue or monolayer of blood cells or other cells, at the area 61 on the slide. The pathologist will then stain or otherwise treat simultaneously the control cell objects and the specimen cell objects for image enhancement. The preferred slides are provided in a kit which have bottles of reagent therein specific to the control cell objects, and herein the kit contains bottles of Feulgen Azure A reagent solution and bottles of rinse reagent solution to specifically and quantatively stain cellular DNA.

The light calibrating material 52 which is in the form of a cross shown in FIG. 4 may also take a large number of different shapes and forms, and in fact, may be merely the border 54 for the control cell objects or may be a logo CAS or other identifying mark which has been applied to the slide to provide a predetermined optical density when the light optics for the microscope are adjusted to the desired intensity. When the operator turns on the microscope 12, the first instructional display on a monitor screen 62 (FIG. 1) is a request for patient labeling, such as the patient's name, hospital, patient number and comments with respect to the test being performed, which information is inserted by the operator using the keyboard 36. This instruction comes from the instrument control logic 22; and after such a labeling operation, the logic 22 places on the screen 62 the request for calibration of the optical lighting 16. This light source calibration achieves a number of results including assistance in focusing the microscope, the providing of an update of a gray scale histogram which may be in the form generally shown in FIG. 7 entitled "Distribution of Light Intensity". The illustrated histogram shows a comparison of incident light $I_o$ and transmitted light $I_t$ with the transmitted light having grey level value of 32 and the incident light having a grey level value of about 195 in this instance, as shown in FIG. 7. The operator views on the TV monitoring screen 62 the light calibration material 45 and a histogram similar to that shown in FIG. 7 is generated by inputing light from a number of locations or picture elements, to form a light source calibration histogram similar to that of FIG. 7, this other histogram being displayed on the program control vidio monitor 62. When the light has been adjusted to provide the left and right peaks $I_t$ and $I_o$ for the transmitted and incidental light at the desired grey levels of 32 and 195, in this instance, the logic of the apparatus then uses the $I_o$ and $I_t$ values to set up an internal calibration table for optical density, such that each picture element sensed is referred to this table to have a known optical density in the image scene being analyzed.

As is known with digital imaging apparatus the actual optical density for a dark object is known using white ($I_o$) as a reference. By calibrating the apparatus for optical density, the incoming data may be converted by the lookup tables in the image processing board 21 so that output shown optical density can be linearly added to proportionately reflect directly, in this instance, the amounts of DNA.

Having calibrated the apparatus for optical density, the control program logic 22 next requests on the monitor 62 a control cell calibration function as shown in the histogram of FIG. 8. During this control cell calibration, the operator moves the microscope stage by turning the conventional X and Y knobs 70 (FIG. 1) to shift the control cell objects 40 into view on the monitoring screen 37. When the individual cell object 40 is within a field box or border 75 (FIG. 1), the operator presses a key on the keyboard 36 to enter measurement of the summed optical density for that control cell object. After a suitable number of control cell objects have been analyzed, the operator will be provided with a histogram such as shown in FIG. 8 on the vidio monitor 62 which shows the operator the control cell object ploidy distribution as having a relative quantity of DNA. Internally within the instrument control logic 22, summed optical density values actually measure for the control cell objects is compared to a predetermined standard or reference amount of DNA which the control cells are known to have. The actual summed optical density found by the operator is divided into the stored reference DNA value to provide a factor by which to adjust for deviation of the stain from a perfect staining for which the internal reference level has been set up.

Either earlier or at this stage in the operation the operator moves the stage to the calibration or reference dot 52 and presses the button to record location of the dot 52 as the zero-zero X and Y coordinate from which the X-Y coordinates of each specimen cell will be located and given an address so that it can later be retrieved by going back to the same coordinates to locate the cell or the cell image which may be called up from stored memory by giving this address.

The operator will now begin cell data acquisition for the DNA ploidy analysis. The operator will select a number of field locations along the slide specimen area 61 for analysis. The operator will move the X and Y knobs 70 for the microscope stage 51 to move into view on the monitoring screen 37 a first field of specimen cell objects to be analyzed for DNA content as well as for cell morphology if desired. The operator will move the field box over a particular specimen cell object 12 being displayed on the monitor 37 and then the operator will use a key to cause the scanning of the pixels (picture elements) of the specimen object to classify the cell in a manner similar to that disclosed in U.S. Pat. No. 4,453,266 to give summed optical density for the cell specimen object i.e., a stained cell nucleus, as well as its area, its roundness, and other classification information. Also, the operator has on the keyboard 36 several cell classification keys to be manually operated and the operator depresses one of the keys to a known category such as normal cell; type 1 cancer cell; a type 2 cancer cell; a type 3 cancer cell; and etc. On the monitoring screen 62 there will be shown the X and Y coordinates for the specimen cell in the field box 80 and there will be a histogram being displayed of cell DNA content. The operator selects a number of cells in each field or area and then moves the microscope stage to position a number of different fields of specimen cells into view and takes and analyses a number of these specimen cells until the operator feels he has a representative sample. A histogram, such as shown in FIG. 9 will at this time be displayed on the monitor screen 62 which shows the number of cells of a particular DNA content and shows the DNA content averages for each of the reference peaks, such as shown in FIG. 9. By depressing a print key, on the keyboard 36 the operator may print out the histogram shown in FIG. 9 on the printer 38. The data for this patient's specimen cells is also stored internally within the computer logic 22 for later recall and comparison with data of any new specimen from the same patient for analysis of the patient's progress or regression.

The particular X and Y location for each cell may be obtained by the use of conventional stepping motor techniques which are well known in the art and which are relatively expensive. Herein the X and Y locations are easily determined for any given location by a novel method and apparatus which includes, as best seen in FIG. 2, an X direction sensing strip 100 which may be fastened to the underside of the microscope stage 51 for movement with the stage 51 past a sensing read head 102, which is secured to a stationary part of the microscope and which reads a sensing scale 104 on the sensing strip and provides a digital output to an interface electronic 106 which provides the X coordinate in digital numbers to the instrument control logic 22 for storing in memory and for displaying on the monitor screen 62. Likewise, a similar strip 110 is fastened to the stage for movement in the Y direction with the stage past a read head 112 which is secured to a stationary part of the microscope so that the read head may read the indicia 114 on the Y strip 110 to provide a digital readout to the interface electronics 106 which supplies digital signals to the instrument control logic 122 for storage of the Y coordinate and for showing the Y coordinate on the video monitor adjacent the X coordinate. Manifestly, the system can be reversed with the read heads fastened to the stage for movement therewith with the scale strips 100 and 110 being mounted stationary to provide digital readouts as the heads move thereacross. The illustrated and preferred strips and heads commonly used as instrument feelers gages, or the like, sold under the trademark "SYLVAC" using magnetic strips and magnetic read heads.

It will be appreciated that the illustrated control logic 22 may be personalized computer such as an IBM personal computer AT which has been programmed to do the cell classification and optical density analysis as fully outlined in U.S. Pat. No. 4,453,266 for the classification of red blood cells. The present invention is particularly useful for red blood cells, red blood cell analysis wherein the hemoglobin content is measured rather than the DNA content as above described. As common in red blood cell work, the red blood cells need not be stained for image enhancement so that the staining calibration step may be eliminated for red blood cells when using the specific wave length of light specified in the aforementioned Bacus patents.

It will also be appreciated that the various calibration steps may be eliminated or combined and done simultaneously rather than done in the order and in the sequence and in the manner described for the preferred embodiment of the invention in making a DNA analysis. The use of the present invention for antigen analysis may include the steps of binding of monoclonal antibodies to the speciman and control cell objects. Later the monoclonal body may be conjugated with an enzyme stain. Also, the monoclonal antibody may be conjugated with a fluorescent material. Then fluorescent stain may be excited at a wave length which excites the fluorescence and then this may be observed at another wave length at which fluorescent emission occurs. When the antigen is made for a particular virus, the control cell specimen objects may be treated with a nucleic acid probe specific for the genome of the virus.

A further use of the present invention is to provide a precise measurement of hemoglobin in actual picograms for calibrating other instruments such as the Coulter counter. In such a process, the control blood cells 40 will have a known predetermined hemoglobin value and the specimen blood cells 12 of unknown hemoglobin value will be placed on the specimen area 61. Then the apparatus will be calibrated to show the histogram for the hemoglobin content of the specimen cells 12.

The present invention is not limited to the above described embodiments but extends to cover other embodiments, not shown or described, but falling with the ambit of the appended claims.

What is claimed is:

1. A method of analyzing cell objects on a support in automatic analyzing apparatus comprising the steps of:
   providing a support means which has previously prepared control calibration material thereon,
   adding specimen cell objects to the support means adjacent the calibation material,
   treating the speciment cell objects and the calibration material at the same time with an image enhancing material,
   calibrating the automatic cell object analyzing apparatus by analyzing the treated calibration material on the support means with light and imaging apparatus and adjusting the apparatus based on the analysis, and
   measuring and analyzing the specimen cell objects on the support means.

2. A method in accordance with claim 1 in which the calibration material is an optical density reference material and in which the calibrating step includes adjusting the optics of the apparatus relative to a reference material of known optical density.

3. A method in accordance with claim 2 including the step of using the calibration material also as a reference location mark to simultaneously provide a reference location for the support means at the time of adjusting the optics.

4. A method in accordance with claim 1 in which the calibration material comprises control cell objects and in which specimen cell objects are cells and in which the step of treating comprises staining the control cell objects and specimen cell objects at the same time.

5. A method in accordance with claim 4 in which the staining step comprises staining DNA in the cells.

6. A method in accordance with claim 5 including the step of staining DNA within the nucleus of specimen and control cells.

7. A method in accordance with claim 1 in which the calibration material comprises control cell objects and including the step of binding the same monoclonial antibodies to the specimen and control cell objects.

8. A method in accordance with claim 7 including the further step treating the control and speciment cells object with an image enhancing material.

9. A method in accordance with claim 8 in which the monoclonial anitbody is conjugated with an eynzme and wherein the treating step comprises applying thereto a substance with which the enzyme reacts to provide image enhancement.

10. A method in accordance with claim 9 wherein the monoclonial antibody binds to estrogen receptors in the specimen and control cell objects.

11. A method in accordance with claim 8 in which the monoclonial antibody is conjugated with a florescent material.

12. A method in accordance with claim 11 including the step of exciting the fluorescent material on the cell objects at a wave length which excites the fluorescence of said material and analyzing by the step of observing at another wave length at which fluorescent emission occurs.

13. A method in accordance with claim 1 in which the analysis is for a particular virus and in which the control calibration material and specimen cell objects are treated with a nucleic acid probe specific for the genome of said virus.

14. An apparatus for automatically analyzing cells of a specimen as set forth in claim 1 wherein said means for analyzing includes:
   means for determining the quantity of DNA contained in a specimen cell.

15. An apparatus for automatically analyzing cells of a specimen as set forth in claim 14 wherein said means for analyzing further includes:
   means for determining the number of cells of the specimen having a relative DNA content.

16. An apparatus for automatically analyzing cells of a specimen as set forth in claim 15 wherein said means for analyzing further includes:
   means for displaying the distribution of cells of the specimen to indicate the number of cells having a relative DNA content over a range of DNA content values.

17. A cell analysis method for determining the mass of a predetermined material from the optical density of specimen cell objects, said method comprising the steps of:
   providing a support with a reference area and a specimen area, the reference area already having a plurality of known refrence cell objects having a known mass of said predetermined material in said reference area;
   adding specimen cell objects of an unknown mass of the predetermined material to said support at said specimen area;
   measuring the optical density of the reference cell objects;
   determining a density factor from said measured reference cell objects and said predetermined stored known mass of said predetermined material of said reference cell objects;
   measuring the optical density of said specimen cell objects; and
   determining the true mass of said predetermined material of said specimen cell objects from said measured optical density of said specimen cell objects and said density factor.

18. A cell analysis method as set forth in claim 17 further comprising the step of:

determining a phyical characteristic of said specimen cell objects from said determined true mass of said predetermined material.

19. A cell analysis method as set forth in claim 18 wherein:
said reference cell objects and specimen cell objects are red blood cell objects and said determined physical characteristic is mean cell hemoglobin.

20. An apparatus for automatically analyzing cells of a specimen as set forth in claim 17 wherein:
said density factor is a factor indicating the change in optical density of the reference cell objects due to the staining process.

21. An apparatus for automatically analyzing cells of a speciment as set forth in claim 20 wherein:
said stain preferentially stains portions of the reference cell objects and the specimen cell objects.

22. An apparatus for automatically analyzing cell objects of a specimen as set forth in claim 17 wherein said means for calibrating includes:
means for displaying the distribution of light intensity from the calibration area of the slide; and
means for adjusting the light source in a direction such that the displayed distribution substantially matches a reference distribution.

23. An apparatus for automatically analyzing cells of a specimen as set forth in claim 22 where said calibration area is divided into pixels each having a light intensity associated therewith, and said means for displaying includes:
means for displaying a range of different light intensities and the number of pixels of said calibration area which have said different intensities.

24. A microscopic slide for an automated cell analysis system having stored known mass characteristics for cell objects and for use in analysis of specimen cell objects, said slide comprising:
a support having a reference area on one side of said support, said reference area containing reference objects thereon having said predetermined known mass characteristics similar to the specimen objects to be analyzed for a true known mass characteristic at a later time, said reference objects to be image enhanced or analyzed at the time the specimen objects are image enhanced or analyzed for calibrating the apparatus.

25. A microscopic slide as set forth in claim 24 wherein said support further includes:
an identification area having a prefixed optical pattern which can be identified by said apparatus for verifying the integrity of the slide.

26. A microscopic slide as set forth in claim 24 wherein said reference area further includes:
a focusing area having an optical pattern of a predetermined optical density which can be measured and identified by said apparatus.

27. A microscopic slide as set forth in claim 25 wherein:
said optical identification pattern can be identified by measuring the physical dimensions between one or more identifiable features of said pattern.

28. A microscopic slide as set forth in claim 24 wherein:
said reference area is delineated by a pattern which can be detected visually.

29. A microscopic slide as set forth in claim 24 wherein said side further includes:
an identifiable feature which acts as a location reference for the automated cell analysis system.

30. A method of analyzing cell objects on a support useable with an automatic cell analyzing apparatus,
providing a support having control cell objects with known characteristics of a predetermined material,
placing specimen cell objects having an unknown amount of such predetermined material on the support,
putting the support in the apparatus for analyzing the cell objects,
performing an integrity check on the support to determine if it is a valid support having the control cell objects of the known characteristics of the predetermined material for calibrating the cell analyzing apparatus,
disabling the apparatus from analysis of the specimen cell objects of the support is not validated,
and enabling analysis of the cell objects for determining the amount of said predetermined material on the support if the support is validated.

31. A method in accordance with claim 30 in which the step of performing the integrity check comprises optical examining the support for a predetermined optical reference.

32. An automated cell analysis system comprising:
a microscope with focusing means;
means for supporting a specimen slide means with specimen cell objects for mounting on said microscope and control cell objects on said slide means having known characteristics of a predetermined material and having at least one physical characteristic distinguishing whether said slide means is authorized for use in the cell analysis system;
said control cell objects having a known mass of said predetermined material in said reference area;
said specimen cell objects having an unknown mass of the predetermined material;
means for measuring the optical density of said predetermined material in said control cell objects;
means for storing a known cell mass for said reference cell objects,
means for determining a density factor from said measured optical density of said predetermined material in said control cell objects and the stored known mass of said predetermined material for said control cell objects;
means for measuring the optical density of said predetermined material in said specimen cell objects; and
means for determining the true mass of said predetermined material of said specimen cell objects from said measured optical density of said specimen cell objects and said density factor.

33. An automated cell analysis system as set forth in claim 32 wherein:
said at least one physical characteristic is an optical pattern identified by analysis of said optical values.

34. An automated cell analysis system as set forth in claim 33 wherein:
said optical pattern is identified by its physical dimensions.

35. An automated cell analysis system as set forth in claim 33 wherein:
said optical pattern is identified by its average optical density.

36. An automated cell analysis system as set forth in claim 33 wherein:

said optical pattern is identified by having a plurality of identifiable features.

37. An automated cell analysis system as set forth in claim 36 wherein:
said optical pattern is identified by the physical dimensions of said identifiable features.

38. An automated cell analysis system as set forth in claim 36 wherein:
said optical pattern is identified by the optical density of said identifiable features 39. An automated cell analysis system as set forth in claim 36 wherein:
said optical pattern is identified by the physical dimensions separating said identifiable features.

40. An automated cell analysis system as set forth in claim 33 wherein:
said at least one physical characteristic is not identifiable without aid of said microscope.

41. An automated cell analysis system as set forth in claim 33 wherein:
said at least one physical characteristic is not identificable without aid of said identifying means.

42. A cell analysis method for determining the optical density of specimen cells, said method comprising the steps of:
providing a slide with a reference area and having on the slide reference cells of a predetermined optical density in said reference area;
adding specimen cells of an unknown optical density to said slide at a said specimen area on said slide;
staining both said reference cells and said specimen cells with the same stain;
measuring the optical density of the stained reference cels;
determining a staining factor from said measured optical density of said stained reference cells and said predetermined optical density of said reference cells;
measuring the optical density of said stained specimen cells; and
determining the optical density of said specimen cells from said measured optical density of said stained specimen cells and said staining factor.

43. A cell analysis method as set forth in claim 42 wherein said step of staining includes the step of:
preferentially staining only certain portions of said reference cells and said specimen cells.

44. A cell analysis method as set forth in claim 43 wherein said step of preferentially staining said reference cells and said specimen cells includes the step of:
preferentially staining the nuclei or contents of the nucleus of said reference cells and said specimen cells.

45. A cell analysis method as set forth in caim 44 wherein:
said specimen cells are nucleated.

46. An appartus for automatically analyzing specimen cells of a specimen side mounted on a microscope illuminated with a light source, said apparatus comprising:
means for analyzing specimen cells and reference material on the specimen slide each having been treated with an image enhancing material;
means for calibrating the light source on the basis of the distribution of light intensity from a calibration area on the slide;
means for analyzing the cells of a specimen on the basis of the distribution of light intensity from a specimen area on the slide; and means for enabling said analyzing means on the basis of the distribution of light intensity from an identification area on the slide.

47. An apparatus for automatically analyzing cells of a specimen as set forth in claim 46 wherein said reference area contains reference cells which further includes:
means for calculating a reference parameter on the basis of the light intensity from the reference area on the slide.

48. An apparatus for automatically analyzing cells of a specimen as set forth in claim 47 wherein:
said reference parameter is used to calibrate said means for analyzing the cells of a specimen.

49. An apparatus for automatically analyzing cells of a specimen as set forth in claim 48 wherein:
said reference cells and said specimen cells are stained with the same stain.

50. An apparatus for automatically analyzing cells of a specimen as set forth in claim 47 wherein:
said reference parameter is a factor indicating the change in optical density of the reference cells due to the staining process.

51. An apparatus for automatically analyzing cells of a specimen as set forth in claim 50 wherein:
said stain preferentially stains portions of the reference cells and the specimen cells.

52. An apparatus for automatically analyzing cells of a specimen as set forth in claim 46 wherein said means for calibrating includes:
means for displaying the distribution of light intensity from the calibration area of the slide; and
means for adjusting the light source in a direction such that the displayed distribution substantially matches a reference distribution.

53. An apparatus for automatically analyzing cells of a specimen as set forth in claim 50 where said calibration area is divided into pixels each having a light intensity associated therewith, and said means for displaying includes:
means for displaying a range of different light intensities and the number of pixels of said calibration area which have said different intensities.

54. An apparatus for automatically analyzing cells of a specimen as set forth in claim 52 wherein:
said reference distribution is indicative of the number of pixels of said calibration area which should exhibit a particular intensity.

55. An apparatus for automatically analyzing cells of a specimen as set forth in claim 46 further including:
means for moving said slide so that different areas on the slide can be analyzed; and
means for determining the location on the slide being analyzed.

56. An apparatus for automatically analyzing cells of a specimen as set forth in claim 55 wherein said means for determining includes:
means for determining a reference location on said slide in accordance with the light distribution of a location area on said slide.

57. A method of measuring the hemoglobin in specimen blood cells by an optical density measuring apparatus, said method comprising the steps of:
providing a slide with control blood cells having a predetermined hemoglobin value,
providing a slide with control blood cells having a predetermined hemoglobin value,
placing on the slide the specimen blood cells, calibrating the optical density apparatus to the known hemoglobin value of the control cells, measuring the optical density of the specimen cells, and providing an output indicative of the hemoglobin value for the specimen blood cells.

58. A method in accordance with claim 57 including the step of the measuring the hemoglobin value of each of the individual specimen cells, and calculating a mean cell hemoglobin for the specimen cells.

* * * * *

REEXAMINATION CERTIFICATE (2353rd)

United States Patent [19]

Bacus

[11] B1 4,741,043

[45] Certificate Issued Aug. 9, 1994

[54] METHOD OF AND APPARATUS FOR IMAGE ANALYSES OF BIOLOGICAL SPECIMENS

[75] Inventor: James W. Bacus, Hinsdale, Ill.

[73] Assignee: Cell Analysis Systems, Inc., Chicago, Ill.

Reexamination Request:
No. 90/003,042, Apr. 30, 1993

Reexamination Certificate for:
Patent No.: 4,741,043
Issued: Apr. 26, 1988
Appl. No.: 794,937
Filed: Nov. 4, 1985

[51] Int. Cl.$^5$ .............................................. G06K 9/00
[52] U.S. Cl. ........................... 382/6; 128/633; 348/79; 348/135; 356/39; 359/397; 359/396; 364/413.1; 364/413.13
[58] Field of Search ..................... 382/6; 358/107; 364/413.08, 413.09, 413.1; 356/39, 40; 206/456; 128/633; 348/79–80; 359/396–398; 424/3; 427/2; 377/10

[56] References Cited

U.S. PATENT DOCUMENTS 4,059,357 11/1977 Klein ................................. 356/243

OTHER PUBLICATIONS

A. M. J. van Driel-Kulker et al., Abstract entitled: "Rapid Automated DNA Measurements Using Image Analysis Methods," presented at the International Conference of the Society for Analytical Cytology X, B18, Asilomar, Calif. (Jun. 1984) (van Driel-Kulker).

N. J. Pressman and G. L. Wied (eds.), "Proceedings of the Second International Conference on the Automation of Cancer Cytology and Cell Image Analysis" Tutorials of Cytology, Chicago, Ill. (1979) (Pressman), particularly.

Tanke et al., "A Special Preparation Technique and a Machine Staining System for Combined Feulgen-DNA Protein Staining in Exfoliative Cytology"(pp. 103–106).

Beyer-Boon et al., "The Applicability of Acriflavine-S-ITS Stain in Urinary Cytology" (pp. 207–211).

van Ingen et al., "Applications of Fluorescent Stains in Automated Cytology Using Television Techniques" (pp. 221–224).

Ploem-Zaaijer et al., entitled "Cytofluorometric and Cytophotometric DNA Measurements of Cervical Smears Stained Using a New Bi-Color Method" (pp. 225–235).

Al et al., "The Leyden Television Analysis System (LEYTAS) for Rapid Screening of Cytological Specimens" (pp. 237–243).

N. Bohm and E. Sprenger, "Fluorescence Cytophotometry: A Valuable Method for the Quantitative Determination of Nuclear Feulgen-DNA" Histochemie 16, 100–118 (1968) (Bohm).

D. C. Allison et al., "Increased Accuracy of Absorption Cytophotometric DNA Values by Control of Stain Intensity," J. Histochem. and Cytochem. 29, 1219–1228 (1981) (Allison).

K. Otto et al., "Components and Results of a New Preparation Technique for Automated Analysis of Cervical Samples," Anal. Quant. Cytol., 1, 127–135 (1979) (Otto).

R. B. Longmore et al., "Nuclear Area and Fuelgen DNA Content of Normal and Abnormal Oral Squares," The International Academy of Cytology Analytical and Quantitative Cytology, vol. 4, No. 1, 33–38 (Mar. 1982).

*Primary Examiner*—Leo H. Boudreau

[57] ABSTRACT

A user interactive system for dynamically testing and evaluating various cells, antigens, or other materials taken from the human body. More specifically, the DNA in specimen cells is analyzed and quantified by image analysis using pattern recognition techniques. The user is provided with a unique slide or support on which there are specimen and reference materials or objects which are simultaneously stained or otherwise image enhanced at the time of analysis.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT

The patentability of claims 24–29, 32–37, 39 and 40 is confirmed.

Claims 1, 7–12, 14–18, 20–23, 30, 38, 41, 42, 46, 57 and 58 are determined to be patentable as amended.

Claims 2–6, 13, 19, 31, 43–45 and 47–56, dependent on an amended claim, are determined to be patentable.

1. A method of analyzing cell objects on a support in automatic analyzing apparatus comprising the steps of:
providing a support means which has previously prepared control calibration material thereon,
adding specimen cell objects to the support means adjacent the [calibation] *calibration* material,
treating the [speciment] *specimen* cell objects and the calibration material at the same time with an image enhancing material,
calibrating the automatic cell object analyzing apparatus by analyzing the treated calibration material on the support means with light and imaging apparatus and adjusting the apparatus based on the analysis, and
measuring and analyzing the specimen cell objects on the support means.

7. A method in accordance with claim 1 in which the calibration material comprises control cell objects and including the step of binding the same [monoclonial] *monoclonal* antibodies to the specimen and control cell objects.

8. A method in accordance with claim 7 including the further step *of* treating the control and [speciment] *specimen* [cells object] *cell objects* with an image enhancing material.

9. A method in accordance with claim 8 in which the [monoclonial] *monoclonal* antibody is conjugated with an [eynzme] *enzyme* and wherein the treating step comprises applying thereto a substance with which the enzyme reacts to provide image enhancement.

10. A method in accordance with claim 9 in which the [monoclonial] *monoclonal* antibody binds to estrogen receptors in the specimen and control cell objects.

11. A method in accordance with claim 8 in which the [monoclonial] *monoclonal* antibody is conjugated with a [floresent] *fluorescent* material.

12. A method in accordance with claim 11 including the step of exciting the fluorescent material on the cell objects at a [wave length] *wavelength* which excites the fluorescence of said material and analyzing by the step of observing at another [wave length] *wavelength* at which fluorescent emission occurs.

14. [An apparatus for automatically analyzing cells of a specimen as set forth] *A method in accordance with* claim 1 wherein said [means for] *step of* analyzing includes:
[means for] determining the quantity of DNA contained in a specimen cell.

15. [An apparatus for automatically analyzing cells of a specimen as set forth] *A method in accordance with* claim 14 wherein said [means for] *step of* analyzing further includes:
[means for] determining the number of cells of the specimen having a relative DNA content.

16. [An apparatus for automatically analyzing cells of a specimen as set forth] *A method in accordance with* claim 15 wherein said [means for] *step of* analyzing further includes:
[means for] displaying the distribution of cells of the specimen to indicate the number of cells having a relative DNA content over a range of DNA content values.

17. A cell analysis method for determining the mass of a predetermined material from the optical density of specimen cell objects, said method comprising the steps of:
providing a support with a reference area and a specimen area, the reference area already having a plurality of known [refrence] *reference* cell objects having a known mass of said predetermined material in said reference area;
adding specimen cell objects of an unknown mass of the predetermined material to said support at said specimen area;
measuring the optical density of the reference cell objects;
determining a density factor from said measured reference cell objects and said predetermined stored known mass of said predetermined material of said reference cell objects;
measuring the optical density of said specimen cell objects; and
determining the true mass of said predetermined material of said specimen cell objects from said measured optical density of said specimen cell objects and said density factor.

18. A cell analysis method as set forth in claim 17 further comprising the step of:
determining a [phyical] *physical* characteristic of said specimen cell objects from said determined true mass of said predetermined material.

20. [An apparatus for automatically analyzing cells of a specimen] *A cell analysis method* as set forth in claim 17 wherein:
said density factor is a factor indicating the change in optical density of the reference cell objects due to the staining process.

21. [An apparatus for automatically analyzing cells of a speciment] *A cell analysis method* as set forth in claim 20 wherein:
said stain preferentially stains portions of the reference cell objects and the specimen cell objects.

22. [An apparatus for automatically analyzing cells objects of a specimen] *A cell analysis method* as set forth in claim 17 wherein said means for calibrating includes] *further comprising the steps of:*
[means for] displaying the distribution of light intensity from the [calibration] *reference* area of the slide; and

[means for] adjusting the light source in a direction such that the displayed distribution substantially matches a reference distribution.

23. [An apparatus for automatically analyzing cells of a specimen] *A cell analysis method* as set forth in claim 22 [where] *wherein* said [calibration] *reference* area is divided into pixels each having a light intensity associated therewith, and said [means for] *step of* displaying includes:

[means for] displaying a range of different light intensities and the number of pixels of said [calibration] *reference* area which have said different intensities.

30. A method of analyzing cell objects on a support useable with an automatic cell analyzing apparatus, providing a support having control cell objects with known characteristics of a predetermined material, placing specimen cell objects having an unknown amount of such predetermined material on the support, putting the support in the apparatus for analyzing the cell objects, performing an integrity check on the support to determine if it is a valid support having the control cell objects of the known characteristics of the predetermined material for calibrating the cell analyzing apparatus, disabling the apparatus from analysis of the specimen cell objects [of] *if* the support is not validated, and enabling analysis of the cell objects for determining the amount of said predetermined material on the support if the support is validated.

38. An automated cell analysis system as set forth in claim 36 wherein:

said optical pattern is identified by the optical density of said identifiable features.

41. An automated cell analysis system as set forth in claim 33 wherein:

said at least one physical characteristic is not [identificable] *identifiable* without aid of said identifying means.

42. A cell analysis method for determining the optical density of specimen cells, said method comprising the steps of:

providing a slide with a reference area and having on the slide *previously prepared* reference cells of a predetermined optical density in said reference area;

adding specimen cells of an unknown optical density to said slide at a said specimen area on said slide;

staining both said reference cells and said specimen cells with the same stain;

measuring the optical density of the stained reference [cels] *cells*;

determining a staining factor from said measured optical density of said stained reference cells and said predetermined optical density of said reference cells;

measuring the optical density of said stained specimen cells; and determining the optical density of said specimen cells from said measured optical density of said stained specimen cells and said staining factor.

46. An [appartus] *apparatus* for automatically analyzing specimen cells of a specimen [side] *slide* mounted on a microscope illuminated with a light source, said apparatus comprising:

means for analyzing specimen cells and reference material on the specimen slide each having been treated with an image enhancing material;

means for calibrating the light source on the basis of the distribution of light intensity from a calibration area on the slide;

means for analyzing the cells of a specimen on the basis of the distribution of light intensity from a specimen area on the slide; and means for enabling said analyzing means on the basis of the distribution of light intensity from an identification area on the slide.

57. A method of measuring the hemoglobin in specimen blood cells by an optical density measuring apparatus, said method comprising the steps of:

providing a slide with control blood cells having a predetermined hemoglobin value,

[providing a slide with control blood cells having a predetermined hemoglobin value,]

placing on the slide the specimen blood cells, calibrating the optical density apparatus to the known hemoglobin value of the control cells, measuring the optical density of the specimen cells, and providing an output indicative of the hemoglobin value for the specimen blood cells.

58. A method in accordance with claim 57 including the [step] *steps* of [the] measuring the hemoglobin value of each of the individual specimen cells, and calculating a mean cell hemoglobin for the specimen cells.

* * * * *